United States Patent
Yasushi et al.

(10) Patent No.: US 7,104,959 B2
(45) Date of Patent: Sep. 12, 2006

(54) APPARATUS AND METHOD FOR ANALYZING HEART-RATE VARIABILITY BASED ON ELECTROCARDIOGRAM INFORMATION

(75) Inventors: Mitsuo Yasushi, Tsurugashima (JP); Masatoshi Yanagidaira, Tsurugashima (JP)

(73) Assignee: Pioneer Corporation, Tokyo-To (JP)

( * ) Notice: Subject to any disclaimer, the term of this patent is extended or adjusted under 35 U.S.C. 154(b) by 554 days.

(21) Appl. No.: 10/647,589

(22) Filed: Aug. 26, 2003

(65) Prior Publication Data

US 2004/0092835 A1    May 13, 2004

(30) Foreign Application Priority Data

Aug. 27, 2002   (JP)   ............................ P2002-246635

(51) Int. Cl.
  *A61B 5/02*   (2006.01)
  *A61B 5/04*   (2006.01)
  *A61B 5/08*   (2006.01)

(52) U.S. Cl. ..................... 600/484; 600/483; 600/509

(58) Field of Classification Search ............... 600/481, 600/483, 484, 529, 500–503, 508–527
  See application file for complete search history.

(56) References Cited

U.S. PATENT DOCUMENTS

| | | | |
|---|---|---|---|
| 5,042,497 A * | 8/1991 | Shapland ..................... | 600/509 |
| 5,902,250 A * | 5/1999 | Verrier et al. ............... | 600/515 |
| 6,480,733 B1 * | 11/2002 | Turcott ....................... | 600/516 |
| 2004/0019289 A1 * | 1/2004 | Ross .......................... | 600/519 |
| 2005/0143668 A1 * | 6/2005 | Lu et al. ..................... | 600/509 |

OTHER PUBLICATIONS

K. Han, J.H. Nagel, B.E. Hurwitz and N. Schneiderman, "Decomposition of Heart Rate Variability by Adaptive Filtering for Estimation of Cardiac Vagal Tone", *Proceedings of the Annual International Conference of the IEEE Engineering in Medicine and Biology Society*, Orlando, FL, U.S., Oct. 31-Nov. 3, 1991, New York, IEEE, US, vol. 13, No. 2 (Oct. 31, 1991), pp. 660-661, XP000348278.

Shaw-Jyh Shin, Walter N. Tapp, Stanley S. Reisman, Member, IEEE, and Benjamin H. Natelson, "Assessment of Autonomic Regulation of Heart Rate Variability by the Method of Complex Demodulation", *IEEE Transactions on Biomedical Engineering*, New York, NY, U.S., vol. 36, No. 2 (Feb. 1989), XP000009587, pp. 274-283.

(Continued)

*Primary Examiner*—Robert L. Nasser
*Assistant Examiner*—Navin Natnithithadha
(74) *Attorney, Agent, or Firm*—Drinker Biddle & Reath LLP

(57) ABSTRACT

A heart-rate variability analysis apparatus comprises an electrocardiogram information detecting unit, heart-rate signal calculating unit, breathing signal calculating unit, and heart-rate-variability information providing unit. Of these, the electrocardiogram information detecting unit detects electrocardiogram information about an object to be diagnosed. The heart-rate signal calculating unit calculates a heart rate signal indicative of a heart rate of the object from the electrocardiogram information. The breathing signal calculating unit calculates, from the heart rate signal, a breathing signal in which a breathing state of the object is reflected. The heart-rate-variability information providing unit provides variability information of the heart rate of the object in which the breathing state of the object is reflected, on the basis of both of the heart rate signal and the breathing signal. Thus, the heart-rate fluctuations can be measure with higher-precision.

13 Claims, 12 Drawing Sheets

OTHER PUBLICATIONS

L. Zhao, S. Reisman, T. Findley, "Derivation of Respiration from Electrocardiogram during Heart Rate Variability Studies", *Computers in Cardiology* (1994), pp. 53-56, XP-002322495.

Task Force of the European Society of Cardiology and the North American Society of Packing and Electrophysiology, Special Report, "Heart Rate Variability Standards of Measurement, Physiological Interpretation and Clinical Use", pp. 1043-1065, XP002236874.

Gary G. Berntson, J. Thomas Bigger, Jr., Dwain L. Eckberg, Paul Grossman, Peter G. Kaufmann, Marek Malik, Haikady N. Nagaraja, Stephen W. Porges, J. Philip Saul, Peter H. Stone, and Maurits W. Van Der Molen, Committee Report, "Heart rate variability: Origins, methods, and interpretive caveats", *Psychophysiology*, Cambridge University Press, U.S.A., vol. 34 (1997), pp. 623-648, XP009045636.

\* cited by examiner

PRIOR ART

APPARATUS AND METHOD FOR ANALYZING HEART-RATE VARIABILITY BASED ON ELECTROCARDIOGRAM INFORMATION

BACKGROUND OF THE INVENTION

The present invention relates to a method and apparatus for analyzing heart-rate variability of an object to be examined on the basis of electrocardiogram information acquired from the object, and a computer-readable program for a computer to analyze the heart-rate variability of the object.

Recently, an analysis on heart-rate variability of an object to be examined has been spotlighted in many fields, such as sports medical check, and health check. This analysis has been known as "heart-rate variability analysis."

One technique for conventional heart-rate variability analysis is proposed as a CDM (Complex Demodulation) technique, which is pictorially illustrated in FIG. 1. As shown in FIG. 1, electrocardiogram information acquired from an object, which is measured by an electrocardiogram measuring device 1, is fed to a peak-to-peak interval detector 2, where a peak to peak interval of an electrocardiogram waveform is detected and data indicative of the peak to peak interval is calculated. The resultant peak-to-peak interval data is fed to a modulator 4, to which sinusoidal waves of 0.3 Hz are also supplied from a sinusoidal-wave generator 3, so that the modulator 4 multiplies the peak-to-peak interval data by the sine wave and the cosine wave to generate intermediate frequency quadrature signals I (In-phase) and Q (Quadrature).

The quadrature signals I and Q are then sent to a demodulator 5, where those signals I and Q are subjected to low-pass filtering at a bandwidth of 0.15 Hz, so that the signals I and Q are demodulated. Based on the demodulated results, a heart-rate fluctuation output device 6 outputs pieces of information indicating fluctuations in the heart rate of the object.

The fluctuations in the heart rate indicate an index of heart-rate variability. The heart-rate variability shows variations in the cardiac cycles attributable to fluctuations in automatic nerve input to the sinoatrial nodes. In general, to analyze the heart-rate variability requires that peak to peak intervals (hereinafter, called RR intervals) in an electrocardiogram waveform be measured.

A mathematical approach to calculating the amplitude of a breathing component included in the heart-rate fluctuations based on the CDM technique will now be described.

It is assumed that a breathing frequency is fr, a phase is $\phi$, and an intermediate frequency is fw. A signal indicating RR intervals affected by the heart-rate fluctuations is expressed by the following formula:

$$y = A^* \sin(2\pi^* fr^* t + \phi),$$

wherein A denotes the amplitude of a breathing component of a heart-rate fluctuation signal, fr denotes a breathing frequency, and t denotes the time.

Local signals generated from the sinusoidal-wave generator 3 can be expressed as follows:

$$\sin(2\pi^* fw^* t) \text{ and } \cos(2\pi^* fw^* t).$$

Multiplying the RR interval signal by the local signals at the modulator 4 produces intermediate frequency signals I and Q, which can be expressed as follows:

$$I = y^* \sin(2\pi^* fw^* t) = \sin(2\pi^* fr^* t + \phi)^* A^* \sin(2\pi^* fr^* t) \text{ and}$$

$$Q = y^* \cos(2\pi^* fw^* t) = \sin(2\pi^* fr^* t + \phi)^* A^* \cos(2\pi^* fw^* t).$$

Using the production relations of trigonometric functions:

$$\sin(x)^* \sin(y) = 1/2^* (\cos(x-y) - \cos(x+y)) \text{ and}$$

$$\cos(x)^* \sin(y) = 1/2^* (\sin(x-y) - \sin(x+y)),$$

The above formulas can be written into:

$$I = 1/2^* A^* (\cos(2\pi^* fw^* t + \phi - fr^* 2\pi^* t) - \cos(2\pi^* fw^* t + \phi + fr^* 2\pi^* t)) \text{ and}$$

$$Q = 1/2^* A^* (\sin(2\pi^* fw^* t + \phi - fr^* 2\pi^* t) - \sin(2\pi^* fw^* t + \phi - fr^* 2\pi^* t))$$

The breathing frequency fr is usually in a range of 0.15 to 0.45 Hz. Thus, if the local signal fw from the sinusoidal-wave generator 3 is 0.3 Hz, the calculation of fw−fr produces an amount of −0.15 Hz to +0.15 Hz, while the calculation of fw+fr produces an amount of 0.45 Hz to 0.75 Hz. This means that it is sufficient that the demodulator 5 has a low-pass filter of which passing bandwidth is 0 to 0.15 Hz and of which cutoff bandwidth is 0.45 to 075 Hz.

Applying a low-pass filter of which passing bandwidth is 0 to 0.15 Hz to the intermediate frequency signals I and Q allows the second terms of the above I and Q formals to be deleted, so that signals IX and QX are produced as follows:

$$IX = 1/2^* A^* (\cos(2\pi^* (fw - fr) t + \phi) \text{ and}$$

$$QX = 1/2^* A^* (\sin(2\pi^* (fw - fr) t + \phi).$$

Since a trigonometric formula of:

$$\sin(x)^* \sin(x) + \cos(x)^* \cos(x) = 1$$

can be used, so that a formula of:

$$(IX)^2 + (QX)^2 = (1/2^* A)^2$$

is established. Hence, $$A = 2^* ((IX)^2 + (QX)^2)^{0.5}$$

is obtained.

FIG. 2 shows various waveforms of signals obtained on the conventional CDM technique. As shown in FIG. 2(A), it is supposed that an input signal indicating the heart-rate variability can be expressed by a sine wave signal of which amplitude is 1 and of which frequency is 0.2 Hz. FIG. 2(B) shows the foregoing 0.3 Hz local signals, whilst FIG. 2(C) shows intermediate frequency signals (I, Q) produced by multiplying the input signal by the local signals.

Further, FIG. 2(D) shows signals (IX, IQ) produced by applying the low-pass filter to the intermediate signals (I, Q), and FIG. 2(E) shows an amplitude component signal calculated based on the low-pass-filtered signals (IX, IQ).

FIG. 3 explains the relationship between a conventional signal component and aliasing noise. As shown in FIG. 3, since the breathing frequency fr is 0.15 to 0.45 Hz and the local signal frequency fw from the sinusoidal-wave generator 3 is 0.3 Hz, the signal ranges from 0 to 0.15 Hz and the aliasing noise is in a range of 0.45 to 0.75 Hz. The low-pass filter to remove this aliasing noise has a low-passing characteristic shown by a dotted line in FIG. 3, in which a passing bandwidth is set to 0.15 Hz and a cutoff bandwidth is set to a range of 0.45 to 0.75 Hz.

FIGS. 4A and 4B show the amplitude and phase characteristics of an actually used conventional low-pass filter. As shown in FIGS. 4A and 4B, an attenuation amount at a cutoff frequency is set to about −22 dB.

As described above, the conventional heart-rate variability analysis based on the CDM technique uses a low-pass filter of which passing bandwidth is 0.15 Hz and of which cutoff bandwidth is 0.45 to 0.75 Hz. That is, since the passing bandwidth of the low-pass filter is as large as 0.15 Hz, ripple noise has frequently been superposed on the amplitude signal, as shown in FIG. 2(E). There is therefore a drawback that signal components other than a frequency indicative of the breathing are mixed, as noise, with the amplitude signal.

Further, when the breathing is disturbed, the conventional heart-rate variability analysis is likely to be affected easily by invasion of non-stationary noise, thus causing a problem that there is more noise due to frequencies other than the breathing frequency. Still further, in such a case, there has been provided no mans for detecting the breathing disturbance, so that it has been impossible to estimate reliability of calculated heart-rate variably.

In addition, the conventional heart-rate variability analysis has encountered another problem that, as understood from FIGS. 4A and 4B, the low-pass filter has no sufficient attenuation in its cutoff frequencies.

SUMMARY OF THE INVENTION

The present invention has been made in view of the above circumstances, and an object of the present invention is therefore to provide an apparatus, method, and computer-readable program, which are directed to heart-rate variability analysis that allows a low-pass filter to be designed in an easier manner and suppresses noise from being mixed in a signal to be measured, with high-precision heart-rate fluctuations achieved.

In order to realize the above object, as one aspect, the present invention provides a heart-rate variability analysis apparatus. This apparatus comprises: an electrocardiogram information detecting unit configured to detect electrocardiogram information about an object to be diagnosed; a heart-rate signal calculating unit configured to calculate a heart rate signal indicative of a heart rate of the object from the electrocardiogram information; a breathing signal calculating unit configured to calculate, from the heart rate signal, a breathing signal in which a breathing state of the object is reflected; and a heart-rate-variability information providing unit configured to provide variability information of the heart rate of the object in which the breathing state of the object is reflected, on the basis of both of the heart rate signal and the breathing signal.

In this basic configuration, it is preferred that the heart-rate signal calculating unit is configured to calculate data indicative of a peak to peak interval in an electrocardiogram wave indicative of the electrocardiogram information.

The data of the peak to peak interval is, for example, data indicative of an interval between two adjacent R-waves appearing in the electrocardiogram wave.

It is also preferred that the heart-rate-variability information providing unit is provided with a breathing number calculating unit configured to calculate a breathing rate of the object from an autocorrelation value of the data indicative of the peak to peak interval in the electrocardiogram wave, a modulator configured to apply quadrature modulation to the data indicative of the peak to peak interval, the quadrature modulation using a modulation signal of which frequency being adjusted depending on the breathing rate, a demodulator configured to demodulate the signal modulated by the modulator, and a heart-rate-variability information outputting unit configured to output, as the heart-rate variability information, a demodulated result from the demodulator.

In the above configuration, preferably, the breathing signal calculating unit is formed into an autocorrelator configured to calculate an autocorrelation value of data indicative of a peak to peak interval in an electrocardiogram wave indicative of the electrocardiogram information. In this case, it is preferred that the apparatus comprises a reliability information outputting unit configured to output the autocorrelation value as information indicative of a reliability of the breathing state of the object.

As another aspect of the present invention, there is provided a heart-rate variability analysis method comprising the steps of: detecting electrocardiogram information about an object to be diagnosed; calculating a heart rate signal indicative of a heart rate of the object from the electrocardiogram information; calculating, from the heart rate signal, a breathing signal in which a breathing state of the object is reflected; and providing variability information of the heart rate of the object in which the breathing state of the object is reflected, on the basis of both of the heart rate signal and the breathing signal.

Still, another aspect of the present invention, there is provided a computer-readable program for analyzing heart-rate variability, the program being executed by a computer provided in a heart-rate variability analysis apparatus, the computer achieving the functions of: electrocardiogram information detecting means for detecting electrocardiogram information about an object to be diagnosed; heart-rate signal calculating means for calculating a heart rate signal indicative of a heart rate of the object from the electrocardiogram information; breathing signal calculating means for calculating, from the heart rate signal, a breathing signal in which a breathing state of the object is reflected; and heart-rate-variability information providing means for providing variability information of the heart rate of the object in which the breathing state of the object is reflected, on the basis of both of the heart rate signal and the breathing signal.

BRIEF DESCRIPTION OF THE DRAWINGS

Other objects and aspects of the present invention will become apparent from the following description and embodiments with reference to the accompanying drawings in which.

DETAILED DESCRIPTION OF THE PREFERRED EMBODIMENTS

Preferred embodiments of an apparatus, method, and computer-readable program for analyzing heart-rate variability of an object to be examined will now be described with reference to FIGS. 5 to 12.

(First Embodiment)

Referring to FIGS. 5 to 11, a first embodiment of the heart-rate variability analysis apparatus will now be described, in which the analysis method and computer-readable program will be explained together in terms of their functions.

Figure 1:
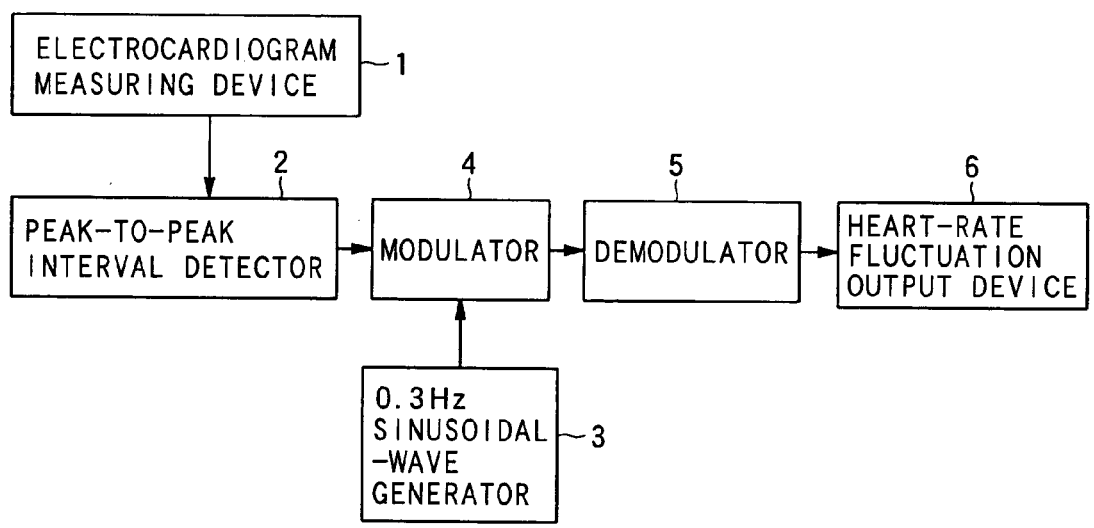
FIG. 1 is a block diagram showing the entire configuration of a conventional heart-rate variability analysis apparatus.
Figure 2A:
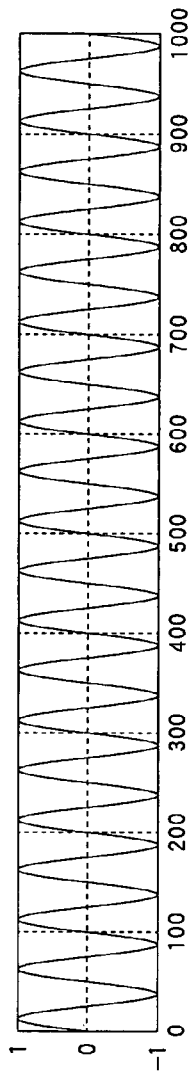
FIGS. 2A to 2E show various waveforms indicative of signals obtained from the conventional heart-rate variability analysis apparatus.
Figure 2B:
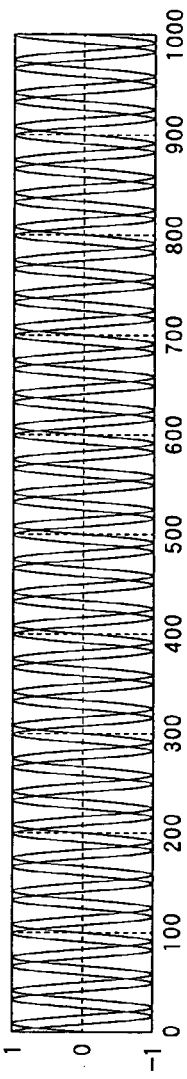
Figure 2C:
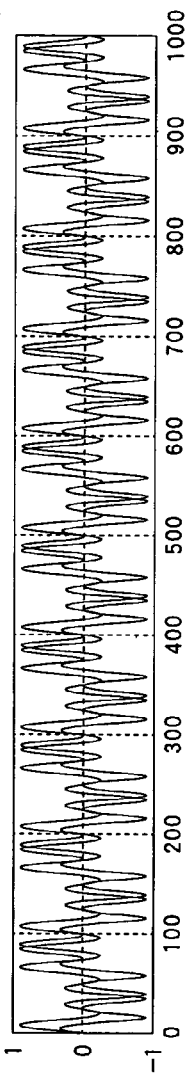
Figure 2D:
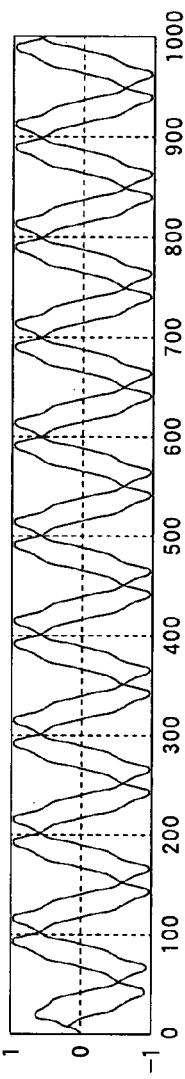
Figure 2E:
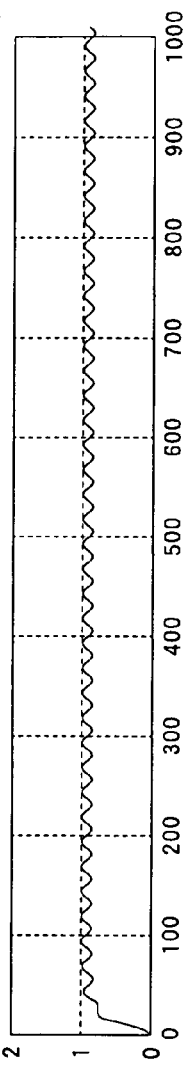
Figure 3:
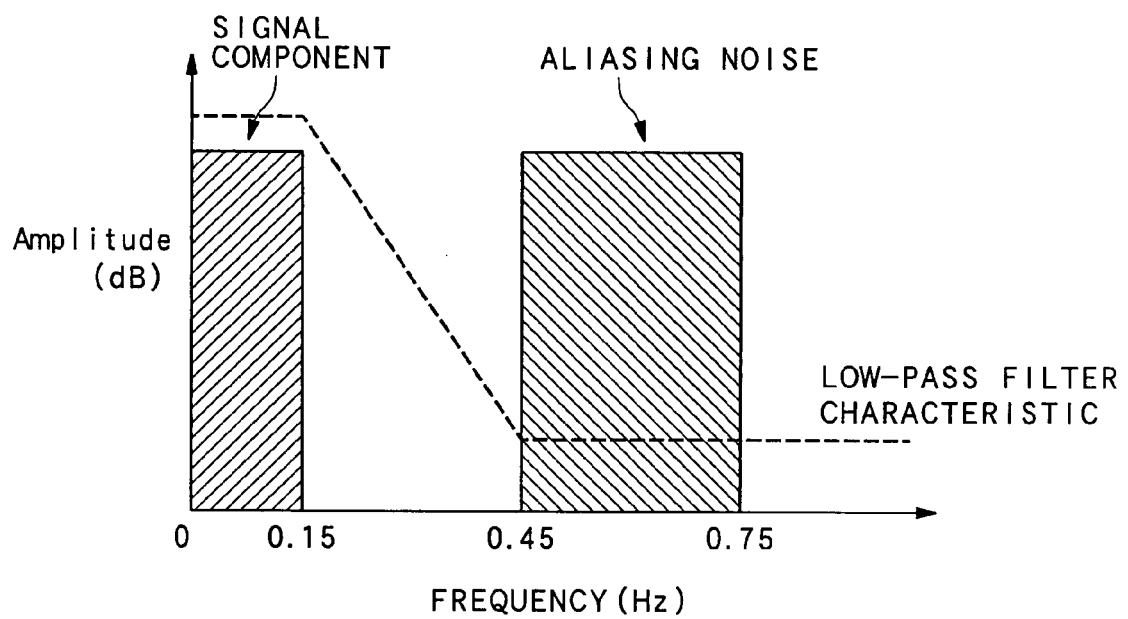
FIG. 3 is a graph explaining the relationship among conventionally used signals, aliasing noise, and a low-pass filtering characteristic.
Figure 4A:
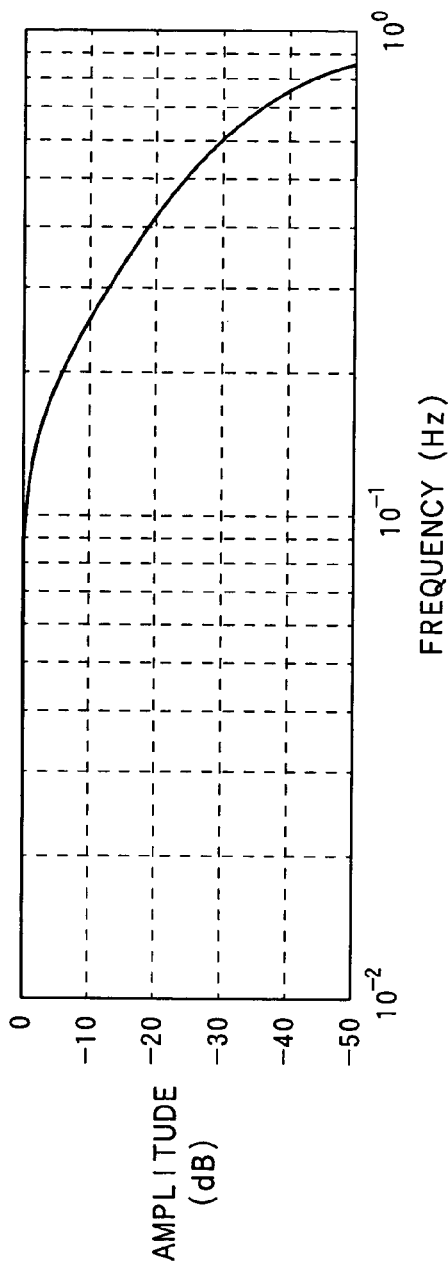
FIGS. 4A and 4B show frequency characteristics of a low-pass filter used by the conventional apparatus.
Figure 4B:
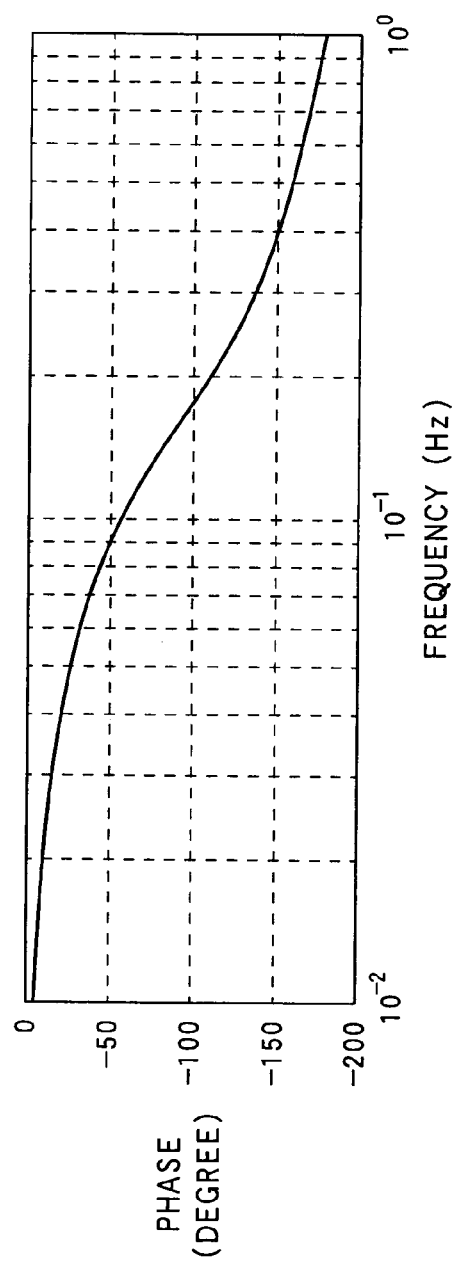
Figure 5:
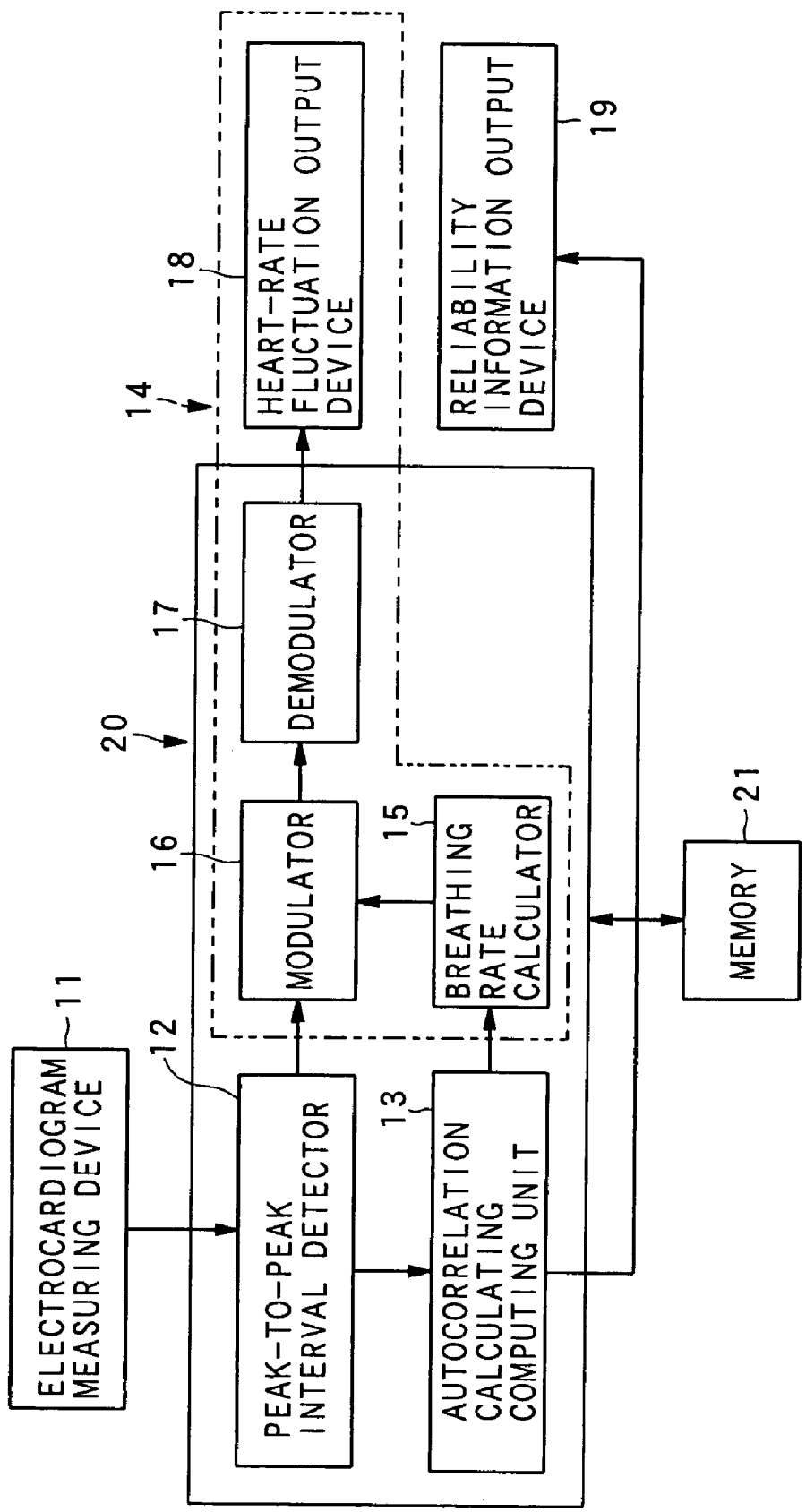
FIG. 5 is a block diagram showing the entire configuration of a heart-rate variability analysis according to a first embodiment of the present invention.

FIG. 5 shows a block diagram of the heart-rate variability analysis apparatus according to the first embodiment. This analysis apparatus is incorporated in a navigation system mounted on vehicles, and used for analyzing the heart-rate fluctuations of a driver who is an object to be examined, analyzed results being used for selecting a type of music, a running route, and/or others depending on driver's mental and physical conditions. In this embodiment, information indicating electrocardiogram of a driver is designed to be detected by an electrocardiogram measuring device of which sensor is embedded in a steering wheel.

As shown in FIG. 5, the heart-rate variability analysis apparatus according to the first embodiment is provided, as essential components, an electrocardiogram measuring device 11, serving as one example of an electrocardiogram-information detecting unit of the present invention, for detecting electrocardiogram information from an object; a peak-to-peak interval detector 12, serving as one example of a heart-rate signal calculating unit of the present invention, for calculating a heart-rate signal indicative of the object's heart rate from the electrocardiogram information coming from the electrocardiogram measuring device 11; an autocorrelation calculating unit 13, serving as one example of a breathing-signal calculating unit of the present invention, for calculating a breathing signal in which an object's breathing condition is reflected based on the heart-rate signal from the peak-to-peak interval detector 12; and a heart-rate-fluctuation information providing unit 14, serving as one example of a heart-rate-fluctuation information providing unit of the present invention, for providing information about object's heart-rate fluctuations in which the object's breathing condition is reflected on the basis of both the heart-rate signal from the peak-to-peak interval detector 12 and the breathing signal from the autocorrelation calculating unit 13.

The peak-to-peak interval detector 12 is means for calculating data indicative of a peak to peak interval of an electrocardiogram waveform providing electrocardiogram information. The peak-to-peak interval data shows temporal intervals (RR intervals) between mutually adjacent two R-waves appearing as part of the electrocardiogram waveform.

The autocorrelation calculating unit 13 is in charge of calculating an autocorrelation value of the RR interval data, that is, peak-to-peak interval data in the electrocardiogram waveform.

The heart-rate-fluctuation information providing unit 14 is provided with a breathing rate calculator 15, serving as one example of a breathing-rate calculating unit of the present invention, for calculating an object's breathing rate from the autocorrelation values of peak-to-peak interval data of an electrocardiogram waveform: a modulator 16, serving as one example of a modulator of the present invention, for applying, to the peak-to-peak interval data, quadrature modulation of which modulation signal is controlled in frequency depending on the object's breathing rate; a demodulator 17, serving as one example of a demodulator of the present invention, for demodulating a modulated signal by the modulator 16; and a heart-rate fluctuation output device 18, serving as one example of a heart-rate fluctuation output device according to the present invention, for outputting heart-rate fluctuation information with the use of demodulated results.

Autocorrelation values of RR interval data computed by the autocorrelation calculating unit 13 are also fed to a reliability information output device 19 serving as one example of a reliability information output device according to the present invention. This output device 19 provides an autocorrelation value as pieces of information showing reliability of an object's breathing condition. In the case that the autocorrelation value is larger than a predetermined threshold of 0.4, it is considered that the breathing is steady, thus being higher reliability in the outputted heart-rate fluctuation information.

Practically, the peak-to-peak interval detector 12, the autocorrelation calculating unit 13, the breathing rate calculator 15, the modulator 16, and the demodulator 17 are composed of a CPU (Central Processing Unit) 20, which transmits and receives various types of data to and from a memory 21. The memory 21 is configured to previously memorize a given computer-readable program which gives souse codes to each component, so that each component is able to operate on the program.

Referring to a flowchart shown in FIG. 6, the processing of the heart-rate variability analysis according to the present invention will now be described. This processing is carried out by the CPU 20 (that is, functionally by the peak-to-peak interval detector 12, the autocorrelation calculating unit 13, the breathing rate calculator 15, the modulator 16, and the demodulator 17).

Figure 6:
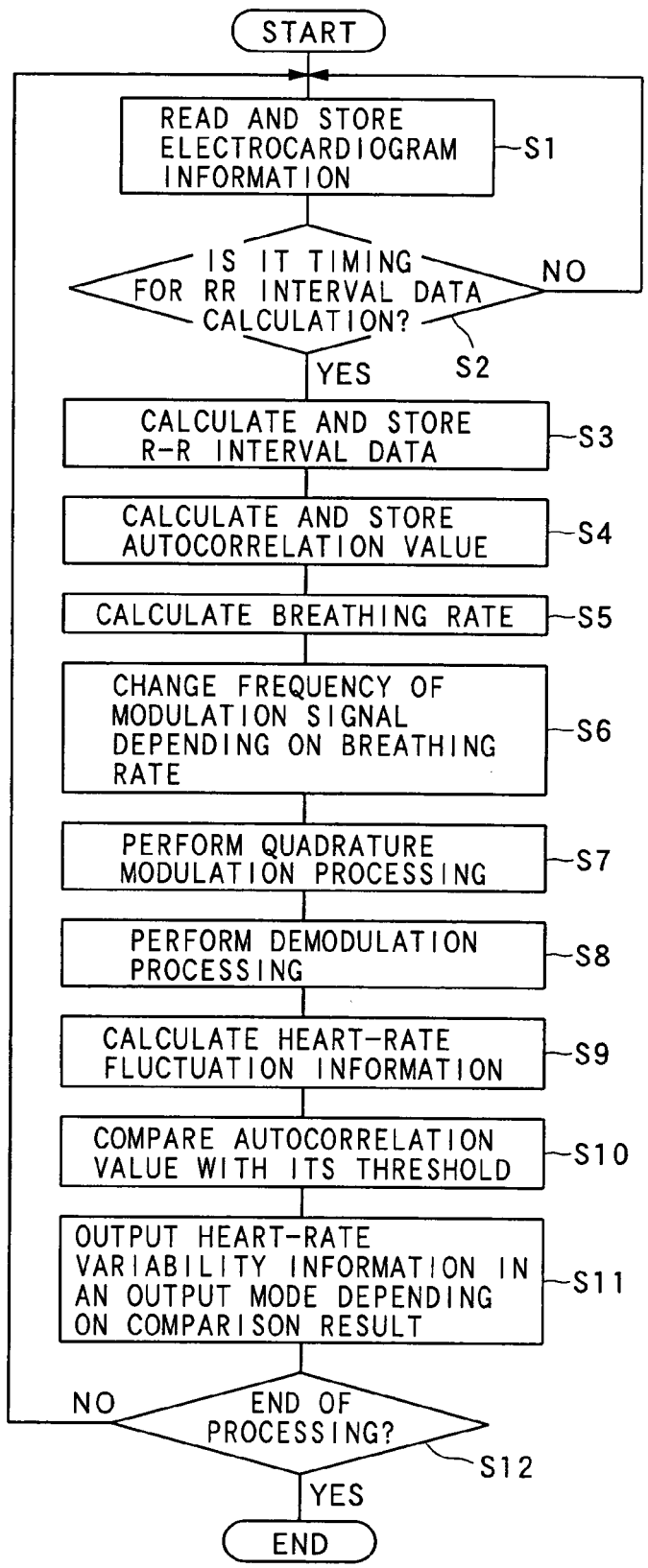
FIG. 6 shows a flowchart for heart-rate variability analysis processing carried out in the first embodiment.

First, electrocardiogram information measured from an object by the electrocardiogram measuring device 11 is taken into the CPU 20, and the electrocardiogram information is stored in the memory 21 (step S1 in FIG. 6). It is then determined whether or not it has come to timing for calculating RR interval data which is peak-to-peak interval data in an electrocardiogram waveform (step S2). When the timing for calculating RR interval data has come (YES at step S2), the processing will proceed to the next step S3, while when such timing has yet to come, the processing is made to return to step S1 to repeat the processing at steps S1 and S2 for waiting the calculation timing.

By the peak-to-peak interval detector 12, RR interval data is then calculated and its calculated results are stored temporality in the memory 21 (step S3). The calculated RR interval data, which is then read out by the autocorrelation calculating unit 13, is subjected to calculation of an autocorrelation value (coefficient) in this calculating unit 13, and its calculated autocorrelation value is stored in the memory 21 (step S4). The thus-calculated autocorrelation values are read out from the memory 21 by the breathing rate calculator 15 so as to be calculated into a breathing frequency (step S5). In this calculation of the breathing frequency, a spline interpolation is carried out with the RR interval data (which is unequally mapped data over the time), and then re-sampling is carried out at 10 Hz.

Based on the breathing frequency calculated above, a modulation frequency for quadrature modulation at the modulator 16 is changed (step S6), and then the modulator 16 applies the quadrature modulation to the RR interval data detected by the peak-to-peak interval detector 12 (step S7). Practically, as the processing at step S7, frequency modulation is carried out by multiplying the RR interval data by two sinusoidal-waves of which phases differ by 90 degrees, thus two frequency-modulated signals (I and Q) being provided to the demodulator 17.

Hence, at the demodulator 17, the two frequency-modulated signals are demodulated such that the signals are low-pass filtered under a low-pass characteristic of a passing band for DC components and a cutoff bandwidth of 0.3 to 0.9 Hz. This demodulation allows a heart-rate fluctuation component to be extracted from the RR interval data, so that the heart-rate fluctuation component is outputted by the heart-rate fluctuation output device 18 (step S9).

Further, at the reliability-information output device 19, the autocorrelation value calculated by the autocorrelation calculating unit 13 is subjected to comparison with a threshold of 0.4, and then the autocorrelation value is displayed under a display mode decided depending on comparison results (steps S10 and S11). In other words, the above comparison makes it possible to determine whether the extracted heart-rate fluctuation component is reliable or not.

Practically, if the calculated autocorrelation value is larger than a threshold of 0.4, it can be recognized that the breathing is steady, whereby it can be considered that the heart-rate fluctuation component outputted by the output device 18 is higher in reliability. A message or others to show such a higher reliability is displayed by the reliability information output device 19.

In contrast, if the calculated autocorrelation value is equal to or smaller than a threshold of 0.4, it can be recognized that the breathing is not steady, whereby it can be considered that the heart-rate fluctuation component outputted by the output device 18 is lower in reliability. A message or others to show such a lower reliability is displayed by the reliability information output device 19. Concretely, the reliability information output device 19 uses different images or audio messages depending on whether the reliability of the heart-rate fluctuation component is higher or lower.

After the processing through the above steps, the CPU 20 determines whether or not the processing should be ended (step S12). In cases where the processing should be ended (YES at step S12), the CPU 20 end the processing, while in cases where the processing needs to be continued (NO at step S12), the processing is returned to step S1 to repeat the foregoing processing.

A mathematical approach to calculate the magnitude of a breathing component in the heart-rate fluctuations, which is employed in the present embodiment, will now be explained.

It is assumed that a breathing frequency is fr, a phase is $\phi$, and an intermediate frequency is fw. A signal indicating RR intervals affected by the heart-rate fluctuations is expressed by the following formula:

$$y = A * \sin(2\pi * fr * t + \phi),$$

wherein A denotes the amplitude of a breathing component of a heart-rate fluctuation signal, fr denotes a breathing frequency, and t denotes the time.

Multiplying an RR interval signal by each of local signals (of which phases differ by 90 degrees) at the modulator 16 produces intermediate frequency signals I and Q, which can be expressed as follows:

$$I = 1/2 * A * (\cos(2\pi * fw * t + \phi - fr * 2\pi * t) - \cos(2\pi * fw * t + \phi + fr * 2\pi * t)) \text{ and}$$

$$Q = 1/2 * A * (\sin(2\pi * fw * t + \phi - fr * 2\pi * t) - \sin(2\pi * fw * t + \phi - fr * 2\pi * t))$$

Because the breathing frequency fr equals the frequency fw of the local signals, the intermediate frequency signals I and Q can be written to:

$$I = 1/2 * A * (\phi) - \cos(2 * 2\pi * fw * t + \phi) \text{ and}$$

$$Q = 1/2 * A * (\phi) - \sin(2 * 2\pi * fw * t + \phi),$$

in which 2*fw is 0.3 to 0.9 Hz. Accordingly, this shows that it is enough to adopt a low-pass filter passing the near DC component and having a cutoff bandwidth of 0.3 to 0.9 Hz.

By applying the low-pass filter of a band passing the DC component to the intermediate frequency signals I and Q, the second term of each of the foregoing formulas can be eliminated, thus producing signals IX and QX which can be written as follows:

$$IX = 1/2 * A * (\cos(2\pi * (fw - fr) * t + \phi) \text{ and}$$

$$QX = 1/2 * A * (\sin(2\pi * (fw - fr) * t + \phi).$$

Using a trigonometric formula of:

$$\sin(x) * \sin(x) + \cos(x) * \cos(x) = 1,$$

the foregoing signals IX and QX can be written to:

$$(IX)^2 + (QX)^2 = (1/2 * A)^2.$$

Hence, there can be provided a formula:

$$A = 2 * ((IX)^2 + (QX)^2)^{0.5}.$$

Therefore, the foregoing consideration gives various waveforms of signals shown in FIG. 7. As shown in FIG. 7(A), it is supposed that an input signal indicating the heart-rate variability can be expressed by a sinusoidal-wave signal of which amplitude is 1 and of which frequency is 0.2 Hz. FIG. 7(B) shows the foregoing 0.2 Hz local signals, whilst FIG. 7(C) shows intermediate frequency signals (I, Q) produced by multiplying the input signal by the local signals.

Figure 7A:
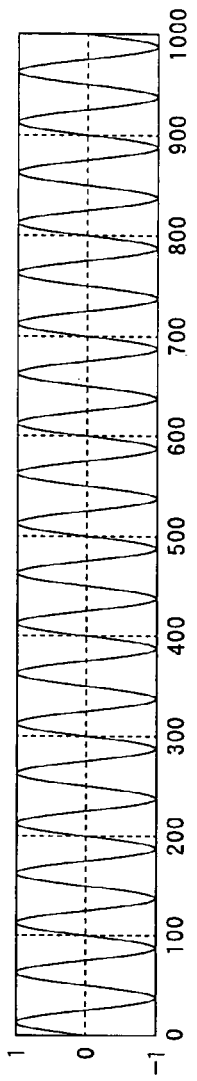
FIGS. 7A to 7E show various waveforms indicative of signals obtained from the heart-rate variability analysis apparatus according to the first embodiment.
Figure 7B:
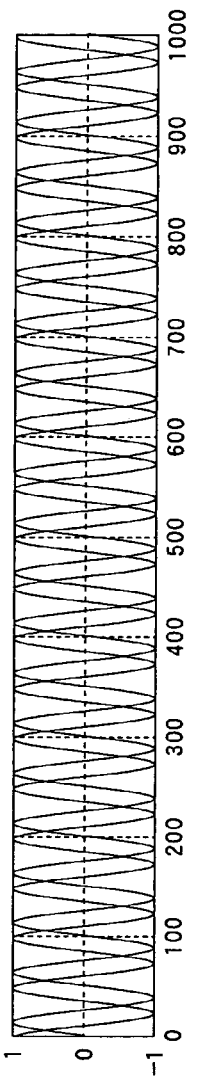
Figure 7C:
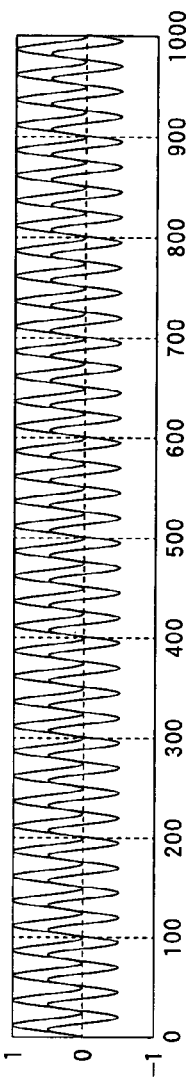
Figure 7D:
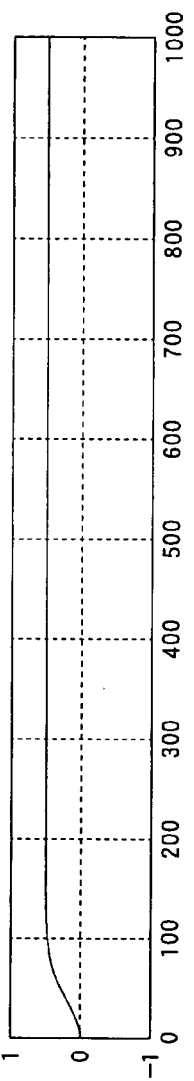
Figure 7E:
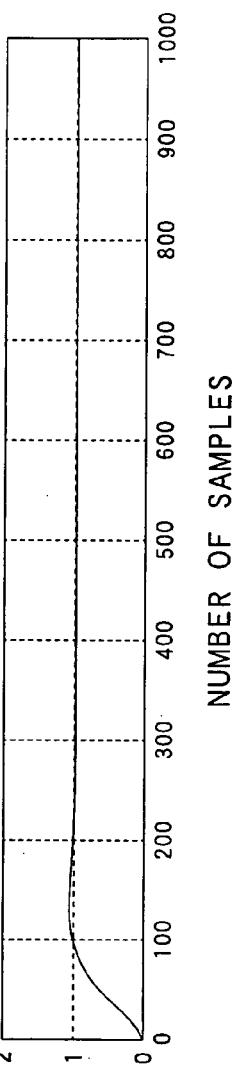

Further, FIG. 7(D) shows signals (IX, IQ) produced by applying the low-pass filer to the intermediate signals (I, Q), and FIG. 7(E) shows an amplitude component signal calculated based on the low-pass-filtered signals (IX, IQ).

Figure 8:
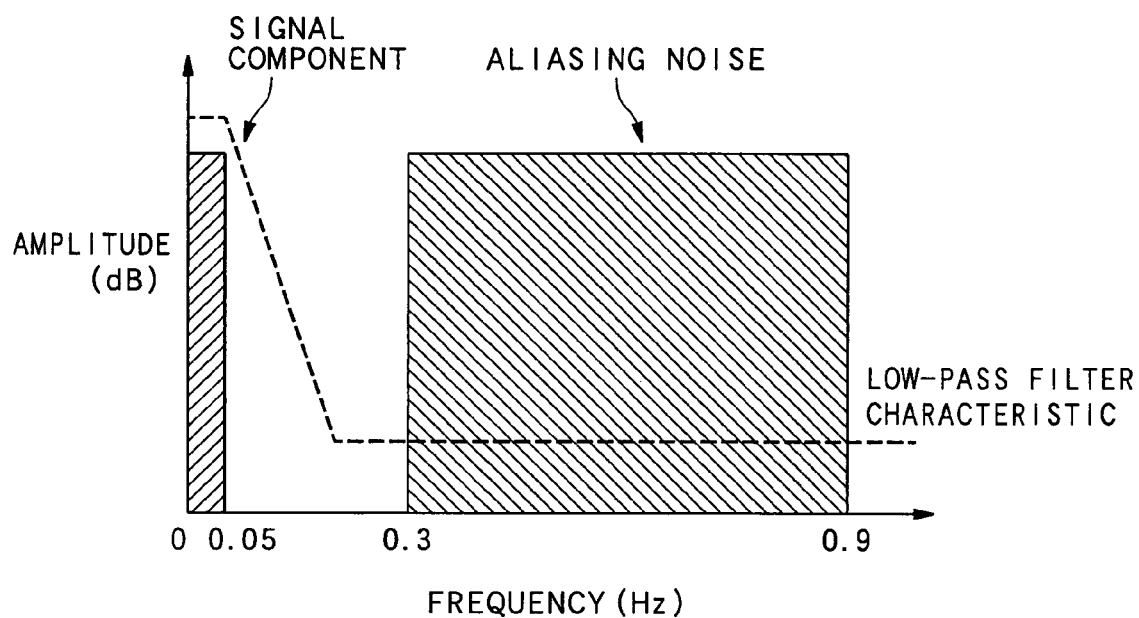
FIG. 8 is a graph explaining the relationship among signals, aliasing noise, and a low-pass filtering characteristic.

FIG. 8 explains the relationship between a signal component and aliasing noise in the present embodiment. As shown in FIG. 8, DC signal components range from 0 to 0.05 Hz, while aliasing noise is in a range of 0.3 to 0.9 Hz. The low-pass filtering characteristic of the low-pass filter placed in a demodulator 17 to remove the aliasing noise is shown by a dotted line in FIG. 8. As clearly understood from FIG. 8, it is sufficient to adopt the passing bandwidth having as narrow as 0.05 Hz, thus making the design of the low-pass filter easier.

Figure 9A:
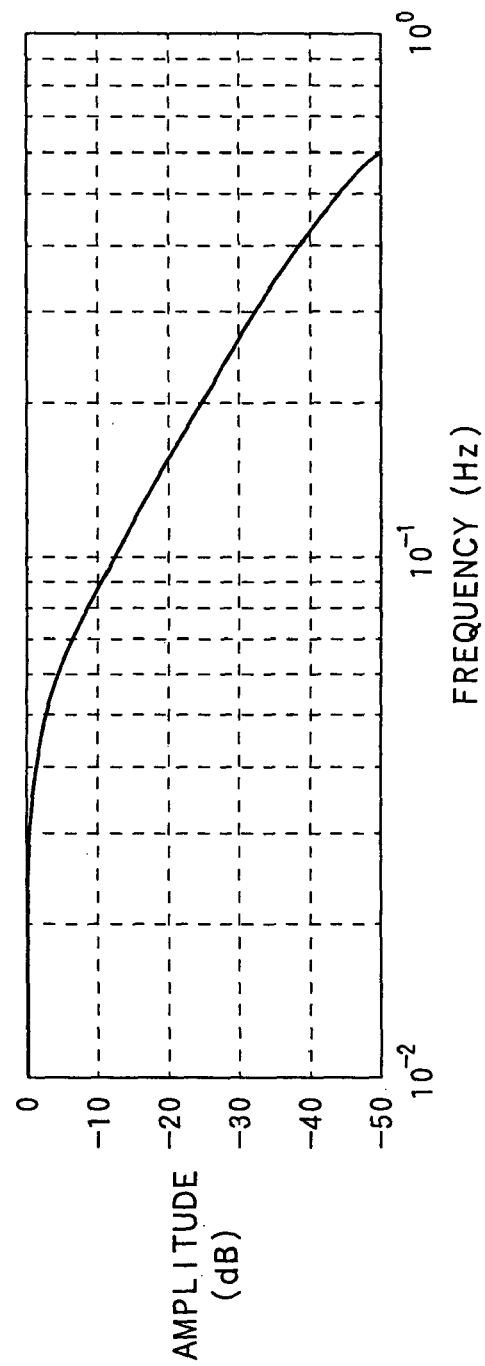
FIGS. 9A and 9B show frequency characteristics of a low-pass filter used by the apparatus according to the first embodiment.
Figure 9B:
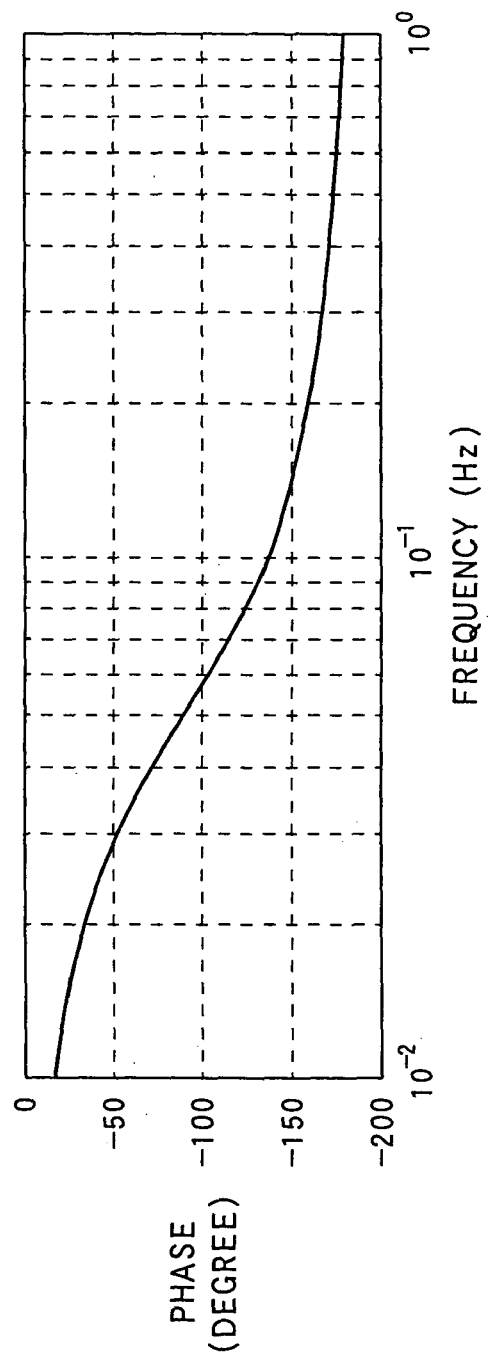

FIGS. 9A and 9B show the amplitude and phase characteristics of a low-pass filer used in the present embodiment, in whish as shown in FIG. 9A, a sufficient attenuation effect can be obtained in the cutoff frequencies.

Figure 10:
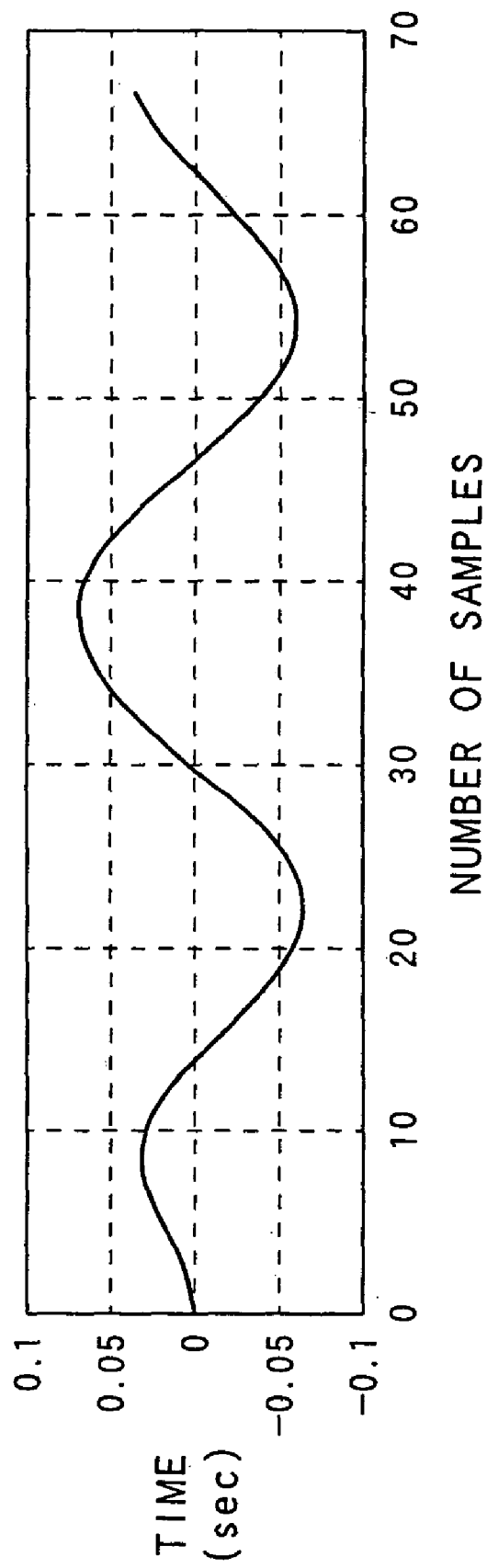
FIG. 10 is a waveform indicative of a heart-rate variability signal handled in the first embodiment.
Figure 11:
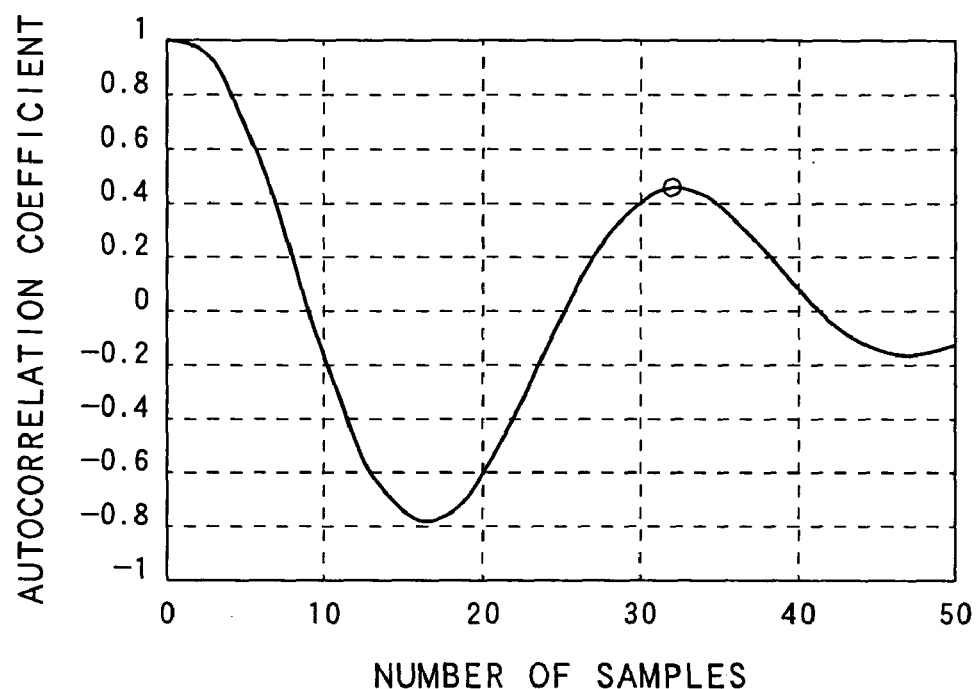
FIG. 11 shows autocorrelation coefficients for an input signal, which is used in the first embodiment.

Estimation of autocorrelation coefficients about the breathing rate will now be explained. FIG. 10 is a waveform showing a heart-rate variability input signal, in which the waveform is 67-point data sampled at 10 Hz. This input signal provides autocorrelation coefficients shown in FIG. 11. As shown in FIG. 11, at a position (delay time) where the number of sampling points is 31, the autocorrelation coefficient is 0.45. Thus a breathing cycle is 3.1 seconds and its frequency is 1/3.1=0.32 Hz, the autocorrelation coefficient is larger than the threshold 0.4. It can be estimated that the breathing is stable.

As described so far, the heart-rate variability analysis apparatus has the electrocardiogram measuring device 11 detecting electrocardiogram information from an object, the peak-to-peak interval detector 12 calculating a heart-rate signal indicative of the object's heart rate from the electrocardiogram information coming from the electrocardiogram measuring device 11, the autocorrelation calculating unit 13 calculating a breathing signal in which an object's breathing condition is reflected based on the heart-rate signal from the peak-to-peak interval detector 12, and the heart-rate-fluctuation information providing unit 14 providing information about object's heart-rate fluctuations in which the object's breathing condition is reflected on the basis of both the heart-rate signal from the peak-to-peak interval detector 12 and the breathing signal from the autocorrelation calculating unit 13. Hence, the design of the low-pass filter can be facilitated and the heart-rate fluctuations can be measured more accurately (thanks to less noise mixed into the heart-rate fluctuation signal to be measured), while there is no necessity of measuring the breathing rate.

Further, in the foregoing embodiment, the peak-to-peak interval detector 12 is configured to calculate data indicative of a peak to peak interval in an electrocardiogram wave indicative of the electrocardiogram information and the data of the peak to peak interval is data indicative of an interval between two adjacent R-waves appearing in the electrocardiogram wave. Thus, using RR interval data enables a high-precision measurement of the heart-rate fluctuations.

Still further, in the foregoing embodiment, the heart-rate-fluctuation information providing unit 14 is provided with the breathing rate calculator 15 calculating an object's breathing rate from the autocorrelation values of peak-to-peak interval data of an electrocardiogram waveform, the modulator 16 applying, to the peak-to-peak interval data, quadrature modulation of which modulation signal is controlled in frequency depending on the object's breathing rate, the demodulator 17 demodulating a modulated signal by the modulator 16, and the heart-rate fluctuation output device 18 outputting information about heart-rate fluctuations using by demodulated results. Hence a low-pass filter used in the modulator 17 becomes easier in its design, while the heart-rate fluctuations can be measured with more precision, with less noise and without measuring the breathing rate.

In addition, in the foregoing embodiment, the autocorrelation calculating unit 13 calculating an autocorrelation value of data indicative of a peak to peak interval (i.e., RR interval data) in an electrocardiogram wave and the reliability-information output device 19 outputting the autocorrelation value as information indicative of a reliability of the breathing state of the object. Thus, it becomes possible that reliability of the obtained heart-rate fluctuation is estimated from the actually measured electrocardiogram information.

(Second Embodiment)

Figure 12:
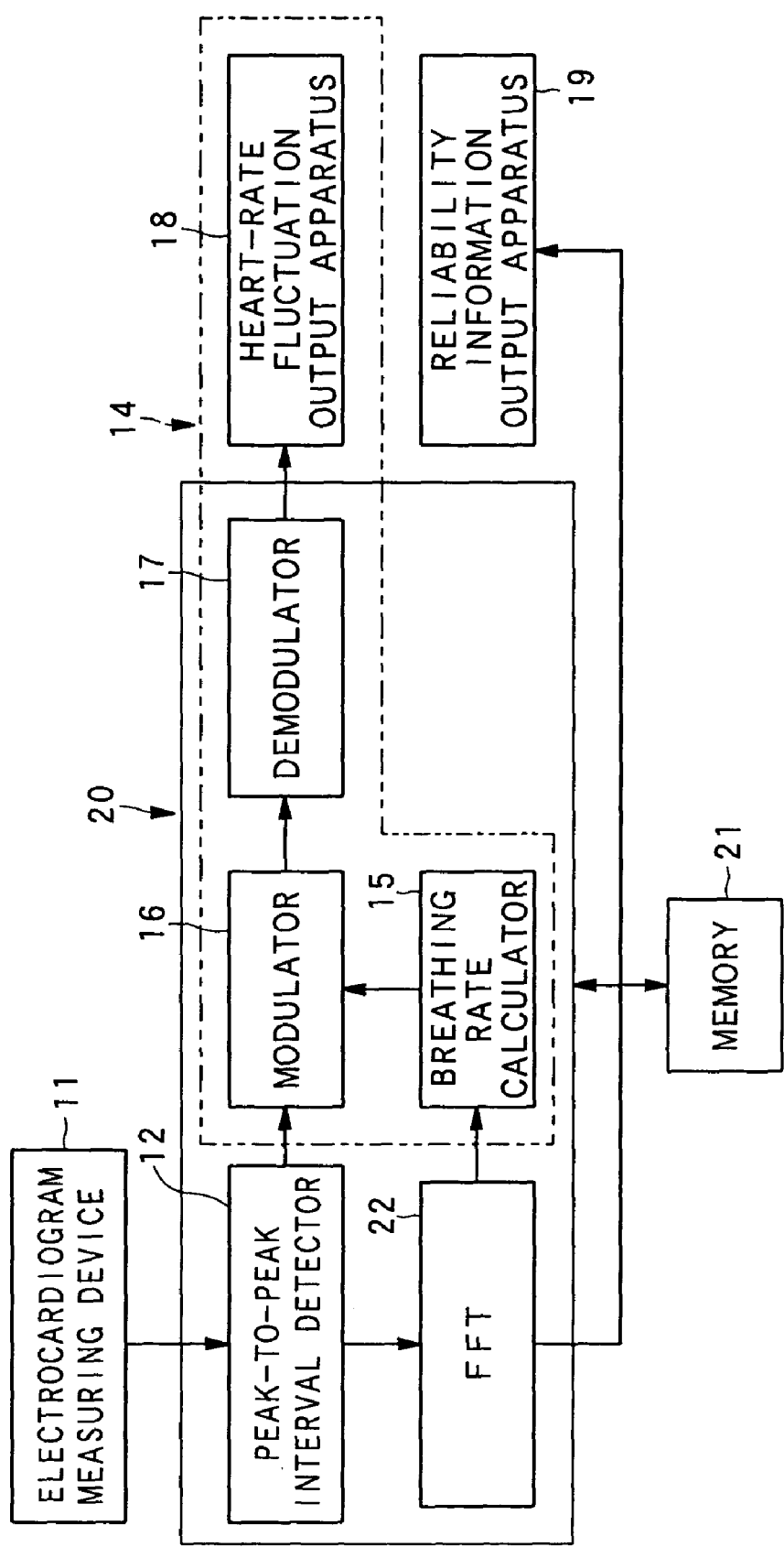
FIG. 12 is a block diagram showing the entire configuration of a heart-rate variability analysis according to a second embodiment of the present invention.

Referring to FIG. 12, a second embodiment of the present invention will now be described. In FIG. 12, for the sake of a simplified explanation, the identical or similar components to those in the first embodiment are represented by the same references as those in the first embodiment.

As shown in FIG. 12, the autocorrelation calculating unit 13 used in the first embodiment (refer to FIG. 5) is replaced by an FFT (fast Fourier Transform) analyzer 22. That is, instead of using the autocorrelation calculating unit 13 to calculate breathing frequencies and its autocorrelation values based on the autocorrelation technique, the FFT analyzer 22 is used to analyze the RR interval data subjected to calculation of a peak frequency. Data of peak frequencies serve as an intermediate frequency signal to be sent to both the breathing-rate calculator 15 and the reliability-information output device 19.

The spectrum analysis of RR interval data in the FFT analyzer 22 provides the similar operations and advantages to those obtained in the first embodiment.

A further modification with regard to the FFT analyzer 22 can be provided. The FFT analyzer 22 can be replaced by a configuration capable of performing spectrum analysis based on a MEM (Maximum Entropy Method) and an AR (autoregression) model. These alternative approaches are able to provide high-resolution and smoothed spectrum data from temporally shorter data compared to the way of using the FFT.

There are some other applications of the present heart-rate variability analysis apparatus. In the foregoing embodiments, the explanation has been given, provided that the heart-rate variability analysis apparatus is applied to communication navigation systems mounted on vehicles in order to analyze driver's heart-rate fluctuations. The heart-rate variability analysis apparatus according to the present invention is not limited to this application, but can be applied to various types of exercise equipment placed in sports gyms, for instance, in order to analyze players' heart-rate fluctuations A modification about storing the program realizing the flowchart shown in FIG. 6 is as follows. The program indicative of the flowchart in FIG. 6 may be stored in information recording mediums, such as flexible disks or hard disks. In this case, a universal type of personal computer may be used to read out the program from such information recording mediums, whereby the personal computer is able to work the same functions as those carried out by the CPU 20 in the foregoing embodiments.

For the sake of completeness, it should be mentioned that the embodiment explained so far is not a definitive list of possible embodiments of the present invention. The expert will appreciate that it is possible to combine the various construction details or to supplement or modify them by measures known from the prior art without departing from the basic inventive principle.

The entire disclosure of Japanese Patent Application No. 2002-246635 filed on Aug. 27, 2002 including the specification, claims, drawings and summary is incorporated herein by reference in its entirety.

What is claimed is:

1. A heart-rate variability analysis apparatus comprising:
   an electrocardiogram information detecting unit configured to detect electrocardiogram information about an object to be diagnosed;
   a heart-rate signal calculating unit configured to calculate a heart rate signal indicative of a heart rate of the object from the electrocardiogram information;

a breathing signal calculating unit configured to calculate, from the heart rate signal, a breathing signal in which a breathing state of the object is reflected; and a heart-rate-variability information providing unit configured to provide variability information of the heart rate of the object in which the breathing state of the object is reflected, on the basis of both of the heart rate signal and the breathing signal.

2. The heart-rate variability analysis apparatus according to claim 1, wherein the heart-rate signal calculating unit is configured to calculate data indicative of a peak to peak interval in an electrocardiogram wave indicative of the electrocardiogram information.

3. The heart-rate variability analysis apparatus according to claim 2, wherein the data of the peak to peak interval is data indicative of an interval between two adjacent R-waves appearing in the electrocardiogram wave.

4. The heart-rate variability analysis apparatus according to claim 2, wherein the heart-rate-variability information providing unit is provided with a breathing number calculating unit configured to calculate a breathing rate of the object from an autocorrelation value of the data indicative of the peak to peak interval in the electrocardiogram wave, a modulator configured to apply quadrature modulation to the data indicative of the peak to peak interval, the quadrature modulation using a modulation signal of which frequency being adjusted depending on the breathing rate, a demodulator configured to demodulate the modulation signal modulated by the modulator, and a heart-rate-variability information outputting unit configured to output, as the heart-rate variability information, a demodulated result from the demodulator.

5. The heart-rate variability analysis apparatus according to claim 1, wherein the breathing signal calculating unit is formed into an autocorrelator configured to calculate an autocorrelation value of data indicative of a peak to peak interval in an electrocardiogram wave indicative of the electrocardiogram information.

6. The heart-rate variability analysis apparatus according to claim 5, further comprising a reliability information outputting unit configured to output the autocorrelation value as information indicative of a reliability of the breathing state of the object.

7. A heart-rate variability analysis method comprising the steps of:

detecting electrocardiogram information about an object to be diagnosed;

calculating a heart rate signal indicative of a heart rate of the object from the electrocardiogram information;

calculating, from the heart rate signal, a breathing signal in which a breathing state of the object is reflected; and providing variability information of the heart rate of the object in which the breathing state of the object is reflected, on the basis of both of the heart rate signal and the breathing signal.

8. The heart-rate variability analysis method according to claim 7, wherein the heart-rate signal calculating step is configured to calculate data indicative of a peak to peak interval in an electrocardiogram wave indicative of the electrocardiogram information.

9. The heart-rate variability analysis method according to claim 8, wherein the data of the peak to peak interval is data indicative of an interval between two adjacent R-waves appearing in the electrocardiogram wave.

10. The heart-rate variability analysis method according to claim 8, wherein the heart-rate-variability information providing step is provided with the sub-steps of:

calculating a breathing rate of the object from an autocorrelation value of the data indicative of the peak to peak interval in the electrocardiogram wave, modulating the data indicative of the peak to peak interval by applying quadrature modulation, the quadrature modulation using a modulation signal of which frequency being adjusted depending on the breathing rate, demodulating the modulated signal, and outputting, as the heart-rate variability information, a demodulated result in the demodulating subs-step.

11. The heart-rate variability analysis method according to claim 7, wherein the breathing signal calculating step is an autocorrelating step of calculating an autocorrelation value of data indicative of a peak to peak interval in an electrocardiogram wave indicative of the electrocardiogram information.

12. The heart-rate variability analysis method according to claim 11, further comprising the step of outputting the autocorrelation value as information indicative of a reliability of the breathing state of the object.

13. A computer including a computer-readable medium for analyzing heart-rate variability, the computer comprising:

electrocardiogram information detecting means for detecting electrocardiogram information about an object to be diagnosed;

heart-rate signal calculating means for calculating a heart rate signal indicative of a heart rate of the object from the electrocardiogram information;

breathing signal calculating means for calculating, from the heart rate signal, a breathing signal in which a breathing state of the object is reflected; and heart-rate-variability information providing means for providing variability information of the heart rate of the object in which the breathing state of the object is reflected, on the basis of both of the heart rate signal and the breathing signal.

* * * * *